(12) United States Patent
Gao et al.

(10) Patent No.: US 12,047,513 B2
(45) Date of Patent: Jul. 23, 2024

(54) LABELING METHOD, APPARATUS, AND DEVICE, AND READABLE STORAGE MEDIUM

(71) Applicant: TENCENT TECHNOLOGY (SHENZHEN) COMPANY LIMITED, Guangdong (CN)

(72) Inventors: Zheng Gao, Guangdong (CN); Yanchun Zhu, Guangdong (CN); Hang Ruan, Guangdong (CN); Jianrong Wu, Guangdong (CN); Jia Chang, Guangdong (CN); Xuan Zhou, Guangdong (CN); Yan Liu, Guangdong (CN); Xiaohui Han, Guangdong (CN)

(73) Assignee: TENCENT TECHNOLOGY (SHENZHEN) COMPANY LIMITED, Guangdong (CN)

( * ) Notice: Subject to any disclaimer, the term of this patent is extended or adjusted under 35 U.S.C. 154(b) by 288 days.

(21) Appl. No.: 17/724,954

(22) Filed: Apr. 20, 2022

(65) Prior Publication Data
US 2022/0247571 A1    Aug. 4, 2022

Related U.S. Application Data

(63) Continuation of application No. PCT/CN2020/124518, filed on Oct. 28, 2020.

(30) Foreign Application Priority Data

Feb. 3, 2020   (CN) .......................... 202010078843.9

(51) Int. Cl.
*H04L 9/32* (2006.01)
*G16H 30/40* (2018.01)

(52) U.S. Cl.
CPC .......... *H04L 9/3247* (2013.01); *G16H 30/40* (2018.01); *H04L 9/3297* (2013.01)

(58) Field of Classification Search
CPC ...... H04L 9/3247; H04L 9/3297; G16H 30/40
See application file for complete search history.

(56) References Cited

U.S. PATENT DOCUMENTS

| 10,715,503 B2 | 7/2020 | Zhang et al. |
| 11,347,565 B1 * | 5/2022 | Johnson ................... G06F 9/54 |

(Continued)

FOREIGN PATENT DOCUMENTS

| CN | 104462738 A | 3/2015 |
| CN | 106302312 A | 1/2017 |

(Continued)

OTHER PUBLICATIONS

International Search Reported dated Jan. 27, 2021 issued in corresponding application PCT/CN2020/124518 (with English translation).

*Primary Examiner* — Beemnet W Dada
(74) *Attorney, Agent, or Firm* — ArentFox Schiff LLP

(57) ABSTRACT

A labeling method is provided. In the method, target image data of a target image is acquired from an offline storage device. The target image data is encrypted based on a first target account. A permission to load the target image data is verified based on a second target account logged in to a labeling client. The target image is loaded in the labeling client in response to the permission to load the target image being verified when the second target account logged in to the labeling client matches the first target account. A label for the target image is received. Further, the label for the target image is transmitted to a server. The server is configured to store the label in association with the target image.

(Continued)

Apparatus and non-transitory computer-readable storage medium counterpart embodiments are also contemplated.

20 Claims, 8 Drawing Sheets

(56) References Cited

U.S. PATENT DOCUMENTS

| | | |
|---|---|---|
| 2014/0219548 A1 | 8/2014 | Wels et al. |
| 2018/0121727 A1* | 5/2018 | Yin .................. G06F 3/011 |
| 2018/0159833 A1 | 6/2018 | Zhang et al. |
| 2019/0220606 A1 | 7/2019 | Li et al. |
| 2020/0020107 A1* | 1/2020 | Kakrania ............ G06T 7/149 |
| 2020/0183880 A1* | 6/2020 | Shah ................. H04L 51/214 |
| 2020/0304475 A1 | 9/2020 | Zhang et al. |

FOREIGN PATENT DOCUMENTS

| | | |
|---|---|---|
| CN | 106682411 A | 5/2017 |
| CN | 106845090 A | 6/2017 |
| CN | 107194267 A | 9/2017 |
| CN | 109686423 A | 4/2019 |

* cited by examiner

LABELING METHOD, APPARATUS, AND DEVICE, AND READABLE STORAGE MEDIUM

RELATED APPLICATIONS

This application is a continuation of International Application No. PCT/CN2020/124518, entitled "LABELING METHOD, APPARATUS, AND DEVICE, AND READABLE STORAGE MEDIUM" and filed on Oct. 28, 2020, which claims priority to Chinese Patent Application No. 202010078843.9, entitled "LABELING METHOD, APPARATUS, AND DEVICE, AND READABLE STORAGE MEDIUM" and filed on Feb. 3, 2020. The entire disclosures of the prior applications are hereby incorporated by reference in their entirety.

FIELD OF THE TECHNOLOGY

Embodiments of this disclosure relate to the field of artificial intelligence, including a labeling method, apparatus, and device, and a computer-readable storage medium.

BACKGROUND OF THE DISCLOSURE

With the development of an artificial intelligence technology, in a process of recognizing a diagnosis result according to a medical image, the medical image may be inputted into a trained recognition model, so as to output a diagnosis result. The recognition model is obtained by training a sample medical image labeled with a diagnosis result. After a doctor labels the medical image, the recognition model is trained by using the labeled medical image, and the to-be-labeled medical image needs to be first transmitted to a terminal used by the doctor.

A doctor labels the medical image in an online labeling manner. After a to-be-labeled medical image is uploaded to a labeling platform, a doctor can load or download the to-be-labeled medical image on the labeling platform, so as to label the image and upload a labeling result to a server for corresponding storage with a labeled medical image.

SUMMARY

Security requirements, along with an amount of data required by the medical images, can reduce an efficiency of the labeling process. For example, while an online labeling process may be easier to secure, due to a data amount of the medical image usually being large, a large amount of time needs to be spent to complete downloading or loading even at a normal network speed to a labeling platform. For example, 100G medical images need to be downloaded or loaded for more than ten or even tens of hours. As a result, labeling can take a relatively long time, and thus labeling efficiency can be relatively low.

Embodiments of this disclosure include a labeling method, apparatus, and device, and a non-transitory computer-readable storage medium, which can improve labeling efficiency of a medical image in a labeling process.

According to one aspect, a labeling method is provided. In the method, target image data of a target image is acquired from an offline storage device. The target image data is encrypted based on a first target account. A permission to load the target image data is verified based on a second target account logged in to a labeling client. The target image is loaded in the labeling client by processing circuitry in response to the permission to load the target image being verified when the second target account logged in to the labeling client matches the first target account. A label for the target image is received. Further, the label for the target image is transmitted to a server. The server is configured to store the label in association with the target image.

According to another aspect, a labeling apparatus is provided. The labeling apparatus includes processing circuitry configured to acquire target image data of a target image from an offline storage device, the target image data being encrypted based on a first target account. The processing circuitry is configured to verify a permission to load the target image data based on a second target account logged in to a labeling client. The processing circuitry is configured to load the target image in the labeling client in response to the permission to load the target image being verified when the second target account logged in to the labeling client matches the first target account. The processing circuitry is configured to receive a label for the target image. Further, the processing circuitry is configured to transmit the label for the target image to a server, the server being configured to store the label in association with the target image.

According to another aspect, a computer device is provided, including a processor and a memory, the memory storing at least one segment of program, and the at least one segment of program being loaded and executed by the processor to implement the labeling method according to any one of the foregoing embodiments of this disclosure.

According to another aspect, a non-transitory computer readable storage medium is provided, storing instructions which when executed by a processor cause the processor to implement the labeling method according to any of the embodiments of this disclosure.

In another aspect, according to an aspect of this disclosure, a computer program product or a computer program is provided, the computer program product or the computer program including computer instructions, the computer instructions being stored in a computer-readable storage medium. A processor of a computer device reads the computer instructions from the computer-readable storage medium, and executes the computer instructions, so that the computer device performs the labeling method provided in any of the implementations.

The technical solutions provided in the embodiments of this disclosure can improve an efficiency of the labeling process. For example, in this disclosure, the target image data is transferred to a terminal in an offline transfer manner. Further, the target image data is signature-encrypted with reference to the target account logged in to the labeling client in the terminal, so that the target image data can be verified and read only when the account logged in to the labeling client is the target account. Accordingly, the transfer efficiency of the target image data is improved in the offline transfer manner. Further, this can avoid a problem that transmission time is too long due to a network speed limitation in an online transfer process, and the signature encryption process improves transfer security of the target image data in the offline transfer process.

BRIEF DESCRIPTION OF THE DRAWINGS

To describe technical solutions in embodiments of this disclosure more clearly, the following briefly introduces the accompanying drawings required for describing the embodiments. The accompanying drawings in the following description show only some embodiments of this disclosure, and a person of ordinary skill in the art may still derive other drawings from these accompanying drawings.

DESCRIPTION OF EMBODIMENTS

Figure 1:
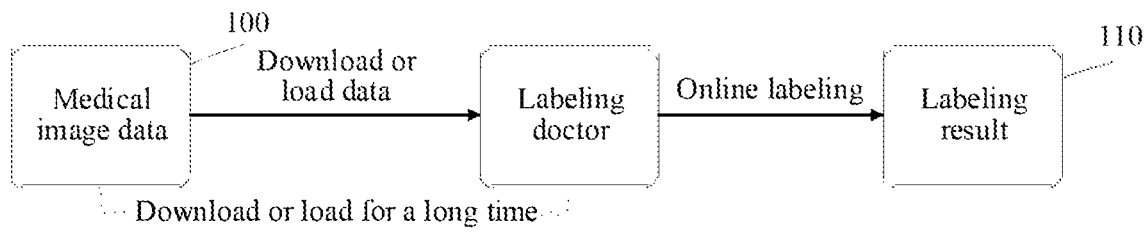
FIG. 1 is a schematic diagram of a process of labeling image data in an online labeling manner according to an exemplary embodiment of this disclosure.

To make objectives, technical solutions, and advantages of this disclosure clearer, the following further describes implementations of this disclosure in more detail with reference to the accompanying drawings.

First, terms involved in the embodiments of this disclosure are briefly introduced.

AI is a theory, method, technology, and application system that uses a digital computer or a machine controlled by the digital computer to simulate, extend, and expand human intelligence, perceive an environment, acquire knowledge, and use knowledge to obtain an optimal result. In other words, the AI is a comprehensive technology of computer science, which attempts to understand essence of intelligence and produces a new intelligent machine that can respond in a manner similar to human intelligence. AI is to study design principles and implementation methods of various intelligent machines, to enable the machines to have functions of perception, reasoning, and decision-making.

The AI technology is a comprehensive discipline and relates to a wide range of fields including both hardware-level technologies and software-level technologies. Basic AI technologies generally include technologies such as a sensor, a dedicated AI chip, cloud computing, distributed storage, a big data processing technology, an operating/interaction system, and electromechanical integration. AI software technologies mainly include several major directions such as a computer vision (CV) technology, a speech processing technology, a natural language processing technology, and machine learning (ML)/deep learning.

ML is a multi-field interdiscipline, and relates to a plurality of disciplines such as the probability theory, statistics, the approximation theory, convex analysis, and the algorithm complexity theory. The ML specializes in studying how a computer simulates or implements a human learning behavior to obtain new knowledge or skills, and reorganize an existing knowledge structure, so as to keep improving its performance. The ML is the core of the AI, is a basic way to make the computer intelligent, and is applied to various fields of AI. The ML and deep learning generally include technologies such as an artificial neural network, a belief network, reinforcement learning, transfer learning, inductive learning, and learning from demonstrations.

Digital signature is, for example, a signature implemented by using a public key encryption technology. A set of digital signatures generally defines two complementary operation manners, one for signature and the other for verification. The digital signature is an application of an asymmetric key encryption technology and a digital digest technology.

In some embodiments of this disclosure, labeling of a medical image is used as an example for description. In a related technology, a medical image may be labeled in an online labeling manner or an offline labeling manner, and the online labeling manner and the offline labeling manner are separately described.

First, the online labeling manner is as follows:

For example, referring to FIG. 1, after medical image data 100 that needs to be labeled by a doctor is uploaded to a labeling platform, the labeling doctor downloads the medical image data 100 from the labeling platform, or the labeling doctor loads the medical image data 100 on the labeling platform. After online labeling is performed on the medical image data 100, a labeling result 110 is generated and stored in the labeling platform, and a training sample of a medical image recognition model is generated according to the labeling result 110 and the medical image data 100.

However, because a data amount of medical image data is generally large, when the data amount of the medical image data reaches hundreds of gigabytes (GB) or several terabytes (TB), it takes a long time to download or load the medical image data, and labeling efficiency is relatively low.

Figure 2:
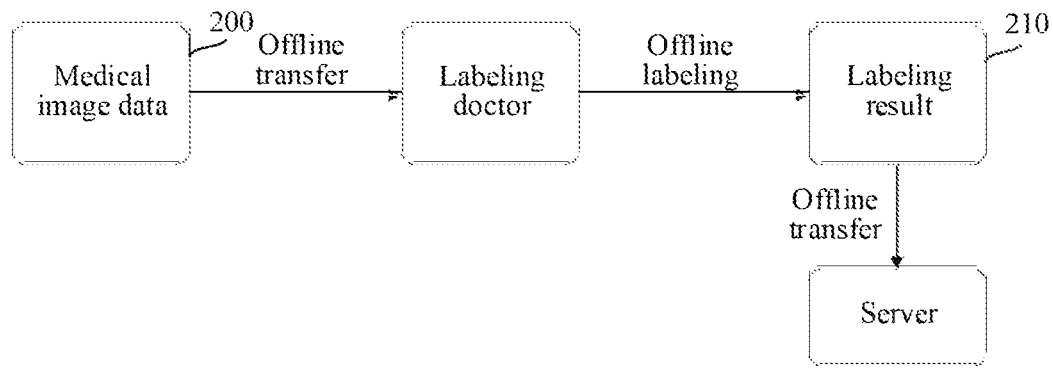
FIG. 2 is a schematic diagram of a process of labeling image data in an offline labeling manner according to an exemplary embodiment of this disclosure.

Second, the offline labeling manner is as follows:

For example, referring to FIG. 2, medical image data 200 that needs to be labeled by a doctor is transferred to the labeling doctor in an offline transfer manner. The labeling doctor labels the medical image data 200 to obtain a labeling result 210, and then stores the labeling result 210 into a server in the offline transfer manner, so as to obtain the medical image data 200 and the corresponding labeling result 210, and obtain a training sample of a medical image recognition model.

However, because the offline labeling manner is used for transferring data by using a hard disk, the labeling result is recorded offline, security of offline data transfer is relatively low, and a risk of data loss is relatively high, thereby reducing labeling security.

In the foregoing description, that the image data is implemented as medical image data is used as an example for description. In an actual operation, the image data may further be implemented as another type of data, such as license plate image data and monitoring image data. This is not limited in the embodiments of this disclosure.

Figure 3:
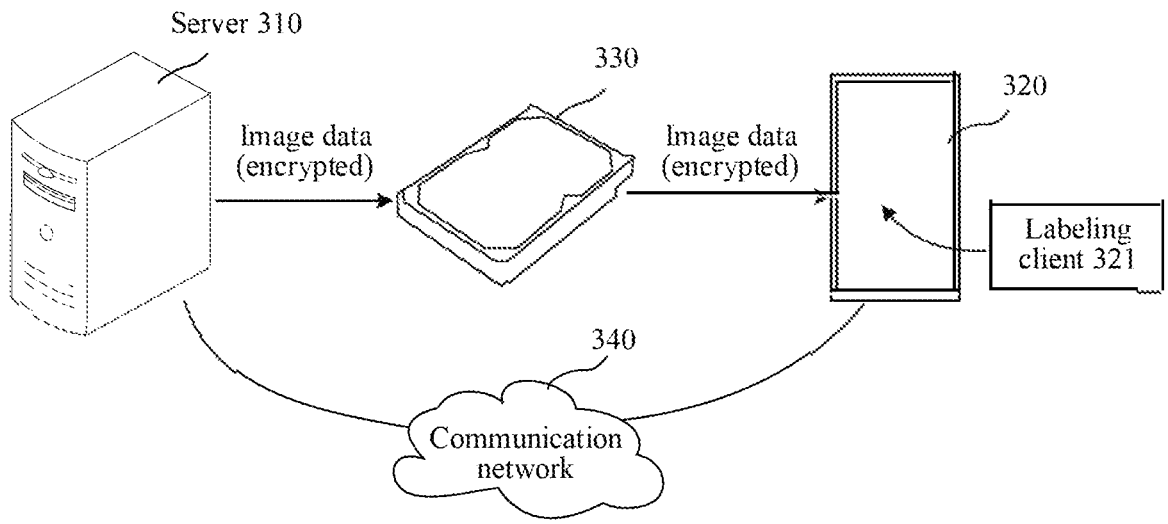
FIG. 3 is a schematic diagram of an implementation environment according to an exemplary embodiment of this disclosure.

For example, FIG. 3 is a schematic diagram of an implementation environment according to an exemplary embodiment of this disclosure. As shown in FIG. 3, the implementation environment includes a server 310, a terminal device 320, and an offline storage device 330.

The server 310 is configured to: generate image data, preprocess the image data, for example, filter processing, desensitization processing, and data structuralization processing. After the preprocessed image data is inputted into the offline storage device 330, the terminal device 320 reads the image data in the offline storage device 330. In some embodiments, the image data inputted into the offline storage device 330 by the server 310 is encrypted in an encryption manner corresponding to a target account.

In an embodiment, a labeling client 321 is installed in the terminal device 320. The target account is logged in to the labeling client 321. After obtaining encrypted image data, the terminal device 320 reads the image data in a decryption manner corresponding to the target account by using the labeling client 321 because the target account is logged in to the labeling client 321, so as to label the image data.

In an embodiment, the terminal device 320 can further connect to the server 310 by using a communications network 340.

In an embodiment, after labeling the image data in the labeling client 321, the terminal device 320 uploads a labeling result to the server 310, and the server 310 correspondingly stores the image data and the labeling result to obtain training sample data of the model.

In an embodiment, the offline storage device 330 may be any device capable of storing information separate and apart from a network or server. For example, the offline storage device 330 can be implemented as a storage device in a form of a removable hard disk, a universal serial bus flash disk (USB flash disk), or the like. Further, the offline storage device 330 can be used to carry out an offline transfer of data between devices, such as between server 310 and terminal device 320.

Figure 4:
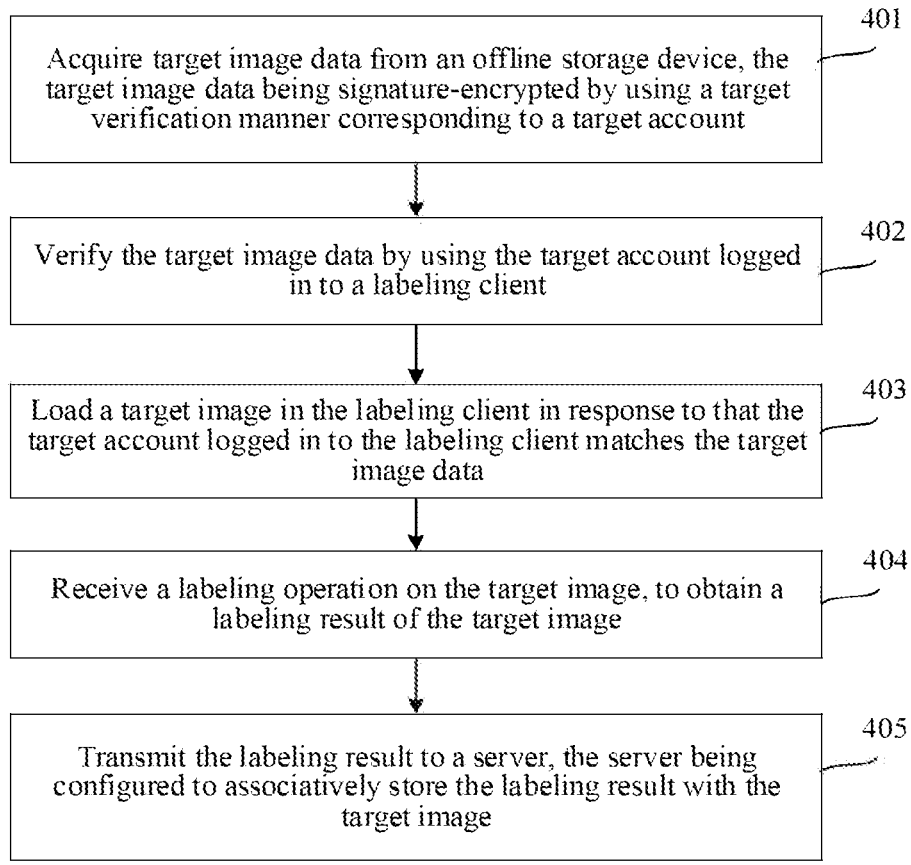
FIG. 4 is a flowchart of a labeling method according to an exemplary embodiment of this disclosure.

For example, FIG. 4 is a flowchart of a labeling method according to an exemplary embodiment of this disclosure. That the method is applied to a terminal is used as an example for description. As shown in FIG. 4, the method con include the following steps.

In step 401, target image data is acquired from an offline storage device, the target image data being signature-encrypted by using a target verification manner corresponding to a target account.

In an embodiment, the target image data is data corresponding to a to-be-labeled target image. After the target image data is encrypted in an encryption manner corresponding to the target account, the target image data is transferred to a current terminal by using the offline storage device.

In an embodiment, the offline storage device may be implemented as a mobile storage device in a form of a removable hard disk, a USB drive, a magnetic tape, or the like. In an embodiment, the target image data is data that is inputted by an image acquiring terminal to the offline storage device, and is used for replacing an online transfer manner to transfer the target image data to the current terminal in an offline transfer manner.

The target image data can be signature-encrypted by using the target verification manner corresponding to the target account. The target image data can be signature-encrypted by using an encryption function. The encryption function has a verification parameter, and the verification parameter is related to the target image and the target account. The verification parameter is inputted into the encryption function, so as to perform signature encryption on the target image data. In an embodiment, after signature encryption is performed on the target image data, a digital signature corresponding to the target image data is obtained. The target image data and the digital signature corresponding to the target image data are acquired from the offline storage device.

The target image data can be image data obtained through preprocessing, and the preprocessing process can include at least one of data filtering, data desensitization, and data structuralization. In an embodiment, after preprocessing, the preprocessed target image data is encrypted and packaged, and is transferred to the current terminal by using the offline storage device.

In step 402, the target image data is verified by using the target account logged in to a labeling client.

In addition to the image data obtained after digital signature encryption is performed on the target image, the target image data further includes a digital signature used when the target image is encrypted. Because a generation manner of the digital signature is related to the target account, and the target account is an account corresponding to a labeling person that is allowed to load the target image, when the labeling person logs in to the labeling client, a target account corresponding to the labeling person's login may be obtained, and the target account is matched with the digital signature in the target image data to verify whether the labeling person has a permission to load the target image.

In an embodiment, the target account is logged in to the labeling client, and the target verification manner corresponding to the target image data is stored in the labeling client. In an embodiment, the target verification manner in which signature encryption is performed on the target image data may be the same as a verification manner stored in the labeling client, or may be a verification manner in a complementary relationship. In this embodiment of this disclosure, an example in which the verification manner stored in the labeling client is the target verification manner is used for description.

That the target verification manner includes the foregoing encryption function is used as an example for description. The labeling client inputs, according to the logged-in target account, the target account and an input parameter corresponding to the target image data into the encryption function, to obtain a verification ciphertext on the labeling client side, and after comparing the verification ciphertext with the digital signature corresponding to the target image data, determines whether the target account matches the target image data.

In an embodiment, for an initiation device that transfers the target image data, because the target image data is data read by a specified target account, when the target image data is signature-encrypted, the digital signature is generated by using a verification parameter related to the target account and the target image. For the current terminal that reads the target image data, because the account logged in to the labeling client is the target account, when the target image data is verified with a signature, the input parameter related to the target account and the target image is inputted into the encryption function, to generate a verification ciphertext, and verify the digital signature.

For example, the target image data is implemented as medical image data, and the target account logged in to the labeling client is an account of the labeling doctor. In an embodiment, because the labeling doctor that labels the medical image data needs to have a corresponding labeling qualification, when a target account of the labeling doctor is registered, a registration code needs to be allocated to the doctor that has the labeling qualification, and the registration code is used as an input parameter for encrypting the medical image data. For example, the registration code may be implemented as a login account of a registered doctor, or may be implemented as another verification code bound to the login account. A communication contact number of the doctor can be bound to the login account, for example, a mobile phone number of the doctor is bound to the login account, and a verification code received by using the communication contact number is used as an input parameter for encrypting the medical image data.

In step 403, the target image is loaded in the labeling client in response to that the target account logged in to the labeling client matches the target image data.

In an embodiment, when the target image data is successfully verified by using the target account logged in to the labeling client, the target image is automatically loaded in the labeling client.

In an embodiment, an automatic loading process of the target image includes any one of the following manners:

First, when the target image data is acquired, the target image data is read to a preset storage location of the terminal, and when the target image is loaded, the target image data is read from the preset storage location, and the target image is loaded.

Second, when the target image data is acquired, the target image data is read to a specified storage location of the terminal, and when the target image is loaded, a read path is set, the target image data is read from the specified storage location, and the target image is loaded.

In step 404, a labeling operation on the target image is received, to obtain a labeling result of the target image.

In an embodiment, the labeling operation is used for labeling the target image, that is, labeling the target image as a labeling result.

For example, the medical image data is used for description. After performing recognition and observation on the target image, the labeling doctor performs a labeling operation, for example, for a gastric medical image, after performing observation on the gastric medical image, the labeling doctor labels "gastritis" as a labeling result of the gastric medical image.

In step 405, the labeling result is transmitted to a server, the server being configured to associatively store the labeling result with the target image.

The labeling result may be used by a non-professional person to determine, according to the target image, a feature represented by the target image, or differentiate between different types of target images. A medical image is used as an example. The labeling result may clearly indicate a disease feature indicated by the medical image or differentiate images corresponding to different case features (for example, gastritis and gastric cancer). It can be understood that the labeling result needs to be used in combination with the target image. Therefore, in a possible implementation, after the labeling person completes labeling of the target image in the labeling client, the terminal may transmit the labeling result back to the server in real time, and the server may associatively store the labeling result with the corresponding target image for various subsequent application scenarios.

Application scenarios for the target image and the corresponding labeling result include a machine learning scenario, a teaching scenario, a medical research scenario, and the like. In the machine learning scenario, to predict an object feature corresponding to the inputted target image data, an image recognition model needs to be pre-trained according to a large quantity of training samples. Therefore, the labeling result and the target image may be generated as training sample data of the image recognition model. In the teaching scenario, the labeling result and the target image may be used as a teaching example. For example, in a medical teaching scenario, medical image data and a disease feature corresponding to the medical image data are used, so that a teacher can correspondingly explain and compare differences between different medical image data. In the medical research scenario, the labeling result and the target image may be used as a research example to analyze features corresponding to different cases.

In an embodiment, after the labeling result is transmitted to the server, the server is configured to perform corresponding matching between the labeling result and the target image, and generate training sample data of the image recognition model to train the image recognition model. In an embodiment, when the image recognition model is trained, the target image is first inputted into the image recognition model to obtain a sample recognition result, compare the sample recognition result with the labeling result labeled by the target account, and adjust a model parameter of the image recognition model by using the comparison result, so as to train the image recognition model.

In a possible application scenario, when the labeling doctor labels the medical image data, the labeling client transmits the labeling result to the server in real time, so that a background user can follow up the labeling progress and evaluate labeling quality in real time, thereby improving accuracy of the labeling result.

In conclusion, in the labeling method provided in this embodiment, the target image data is transferred to a terminal in an offline transfer manner, and the target image data is signature-encrypted with reference to the target account logged in to the labeling client in the terminal, so that the target image data can be verified and read only when the account logged in to the labeling client is the target account, and transfer efficiency of the target image data is improved in the offline transfer manner. This avoids a problem that transmission time is too long due to a network speed limitation in an online transfer process, and the signature encryption process improves transfer security of the target image data in the offline transfer process.

Figure 5:
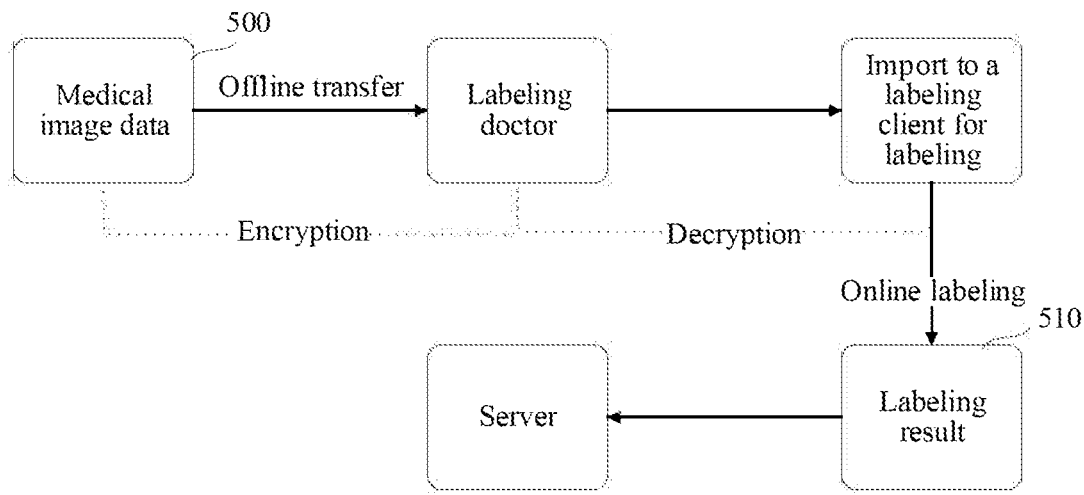
FIG. 5 is a schematic diagram of a transfer process of medical image data according to an exemplary embodiment of this disclosure.

For example, referring to FIG. 5, that the target image data is implemented as medical image data is used as an example for description. FIG. 5 is a schematic diagram of a transfer process of medical image data according to an exemplary embodiment of this disclosure. As shown in FIG. 5, when medical image data 500 is transferred to a labeling doctor in an offline transfer manner, the medical image data 500 is encrypted in a signature encryption manner. After the labeling doctor decrypts the encrypted medical image data 500, the medical image data 500 is transmitted to a labeling client for online labeling, and a labeling result 510 is obtained. The labeling result 510 is transmitted to a server for storage, and training sample data of an image recognition model is generated.

Figure 6:
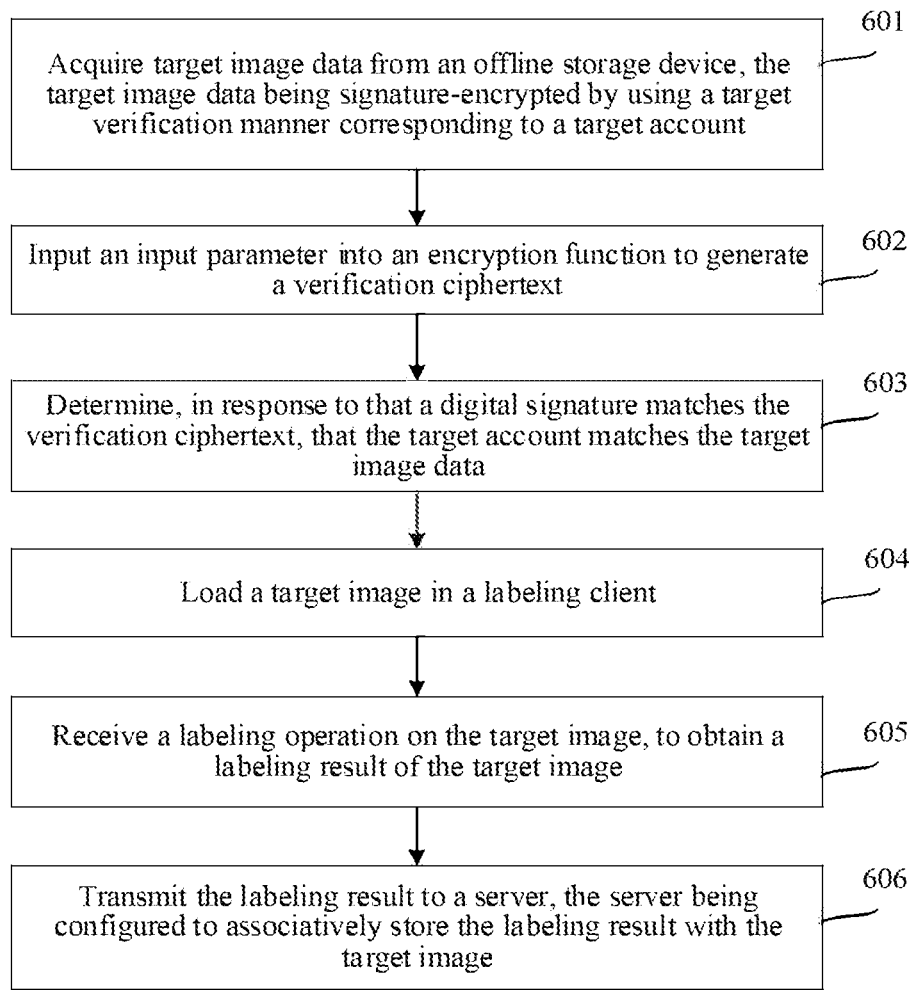
FIG. 6 is a flowchart of a labeling method according to another exemplary embodiment of this disclosure.

In an embodiment, the target image data is encrypted by using an encryption function, and after the target image data is encrypted by using the encryption function, a corresponding digital signature is acquired. FIG. 6 is a flowchart of a labeling method according to another exemplary embodiment of this disclosure. That the method is applied to a terminal is used as an example for description. As shown in FIG. 6, the method can include the following steps.

In step 601, target image data is acquired from an offline storage device, the target image data being signature-encrypted by using a target verification manner corresponding to a target account.

In an embodiment, the target image data is data corresponding to a to-be-labeled target image. After the target image data is encrypted in an encryption manner corresponding to the target account, the target image data is transferred to a current terminal by using the offline storage device.

In an embodiment, the target image data is signature-encrypted by using the target verification manner corresponding to the target account. The target image data can be signature-encrypted by using an encryption function. The encryption function has a verification parameter, a read account specified according to the target image data is the target account, and the verification parameter is related to the target image and the target account. The verification parameter is inputted into the encryption function, so as to perform signature encryption on the target image data. In an embodiment, after signature encryption is performed on the target image data, a digital signature corresponding to the target image data is obtained. The target image data and the digital signature corresponding to the target image data are acquired from the offline storage device.

In an embodiment, because security problems such as loss and easy copying of the target image data may easily occur in the offline transfer process of the target image data, sensitive information in the target image data is disclosed. To further improve security of the target image data, in a possible implementation, the target image data is implemented by preprocessing before offline transfer of the target image data, where the preprocessing process includes at least one of data filtering, data desensitization, or data structuralization. In an embodiment, after preprocessing, the preprocessed target image data is encrypted and packaged, and is transferred to the current terminal by using the offline storage device.

In some embodiments, data filtering means that data that is not qualified or does not meet a labeled target is filtered out through data cleaning. In an embodiment, based on a related machine learning algorithm, dimension reduction is performed on the image data by using a principal components analysis (PCA) technology, the data is clustered with a cosine similarity in vector space, and a threshold is set to filter an image whose edge is abnormal, so as to complete data filtering. Image data that meets a condition is filtered according to a labeling condition of the data. For example, an image whose layer thickness is less than 5 mm is selected according to a thickness of a computed tomography (CT) image, and target image data that meets the labeling condition can be selected through data filtering of the image data, so as to avoid a subsequent labeling process of invalid image data, thereby improving efficiency of acquiring an effective training sample.

Data desensitization refers to performing a desensitization operation on sensitive information. For medical image data, sensitive information such as a patient name and a social security card number are usually reserved. In an embodiment, through data desensitization, only information of value to the labeling process is reserved, such as an identifier and a layer thickness.

For other sensitive information, such as a patient name, encryption desensitization may be performed based on an asymmetric encryption algorithm, a ciphertext is overwritten, and a private key is retained in the server, so as to ensure that data is traceable, and prevent data from being intercepted. Data desensitization is performed on the image data, so that privacy information of the user is not involved in the target image data that is transferred offline or online, thereby avoiding a threat to resource security of the user after the target image data is illegally intercepted, thereby improving security in an image labeling process.

A manner used for data desensitization may further include: replacing a real value with virtual data; replacing the real value with random data; using random displacement change data or the like. This embodiment of this disclosure sets no limitation thereto.

Data structuralization processing refers to structured storage of the processed target image data according to a preset data structure. In a labeling process, a large quantity of image data needs to be labeled and stored. In a subsequent medical image recognition and diagnosis process, different types of labeled image data may be required, and different label requirements may exist for different types of image data. Therefore, to distinguish between different types of image data or different label requirements, the image data may be stored according to a preset data structure, and it is convenient to separately label or use the image data subsequently. The preset data structure may be stored according to an image data category, or may be stored according to different labeling requirements, or may be stored according to corresponding labeling personnel of different levels. This is not limited in this embodiment of this disclosure.

In step 602, an input parameter is input into an encryption function to generate a verification ciphertext.

In an embodiment, the target verification manner includes an encryption function, and the encryption function is a function that is consistent between an encryption end and a verification end, that is, an encryption terminal of the target image data and a labeling client (verification end) store the same function. In the encryption terminal of the target image data, a verification parameter exists in the encryption function, and the verification parameter is related to a target account specified to read the target image data and the target image data itself. In the labeling client, the encryption function corresponds to the input parameter. The input parameter is related to the target account logged in to the labeling client and the target image data. Only when the specified read account of the target image data is consistent with the account logged in to the labeling client, the target image can be loaded in the labeling client.

In an embodiment, the input parameter includes at least one of an account parameter corresponding to the target account and an image parameter corresponding to the target image data, where the account parameter includes at least one of a registration code of the target account and a verification code for a target account to bind a communication contact number, the registration code of the target account is a character code pre-allocated to the target account, and the registration code may be directly implemented as an account identifier of the target account, or may be implemented as a character code bound to the account identifier. The communication contact number bound to the target account may be a mobile number bound to the target account, an email address bound to the target account at any time, or an account of another application program bound to the target account. This is not limited in this embodiment of this disclosure.

In an embodiment, the image parameter includes at least one of a generation timestamp of the digital signature corresponding to the target image data and a digest value of the target image data. The digest value is an MD5 message digest algorithm value of the target image data.

In an embodiment of this disclosure, for example, the input parameter includes the account parameter and the image parameter, the account parameter includes the registration code of the target account and the verification code for the target account to bind the communication contact number, and the image parameter includes the generation timestamp of the digital signature and the digest value of the target image data; and the registration code of the target account, the verification code for the target account to bind the communication contact number, the digest value of the target image data, and the generation timestamp of the digital signature are inputted into the encryption function to obtain the verification ciphertext.

Correspondingly, in this embodiment of this disclosure, when the image data is encrypted in the encryption terminal, the encryption function is obtained in advance, and the verification parameter (corresponding to the input parameter) correspondingly exists in the encryption function; and the registration code of the target account, the verification code for the target account to bind the communication contact number, the digest value corresponding to the target image data, and the generation timestamp of the data signature are inputted into the encryption function to obtain the digital signature corresponding to the target image data.

For example, the target image data is implemented as medical image data. A verification ciphertext is obtained by using an encryption function Y=F(X, DRSA, T, MD5), where Y is a generated verification ciphertext, F is used for indicating the encryption function, X is used for indicating a verification code of a doctor's mobile phone, DRSA is used for indicating a registration code of the doctor, T is a verification timestamp, and MD5 is the digest value of the target image data.

In step 603, in response to the digital signature matching the verification ciphertext, the target account is determined to match the target image data.

In an embodiment, when the digital signature is consistent with the verification ciphertext, it is determined that the target account matches the target image data, that is, the target image data can be read by using the labeling client to which the target account is logged in.

In step 604, the target image is loaded in the labeling client.

In an embodiment, when the target image data is successfully verified by using the target account logged in to the labeling client, the target image is automatically loaded in the labeling client.

In step 605, a labeling operation on the target image is received, to obtain a labeling result of the target image.

In an embodiment, the labeling operation is used for labeling the target image, that is, labeling the target image as a labeling result.

In step 606, the labeling result is transmitted to a server, the server being configured to associatively store the labeling result with the target image.

In an embodiment, the labeling result may be transmitted to the server in an online transmission manner, or may be transferred to the server in an offline transfer manner. When the labeling result is transmitted to the server in the online transmission manner, a correspondence between the labeling result and the identifier of the target image data is transmitted to the server, and the server matches the labeling result with stored target image data according to the correspondence. When the labeling result is transmitted to the server in the offline transmission manner, after the target image data and the corresponding labeling result are matched, the labeling result is transferred to the server by using the foregoing offline storage device.

In conclusion, in the labeling method provided in this embodiment, the target image data is transferred to a terminal in an offline transfer manner, and the target image data is signature-encrypted with reference to the target account logged in to the labeling client in the terminal, so that the target image data can be verified and read only when the account logged in to the labeling client is the target account, and transfer efficiency of the target image data is improved in the offline transfer manner. This avoids a problem that transmission time is too long due to a network speed limitation in an online transfer process, and the signature encryption process improves transfer security of the target image data.

According to the method provided in this embodiment, the target image data is signature-encrypted by using the encryption function, and the input parameter of the encryption function includes the account parameter corresponding to the target account. Therefore, it is ensured that only when the account logged in to the labeling client is consistent with the specified read account of the target image data, the labeling client can load the target image, thereby improving transmission security of the target image data.

Figure 7:
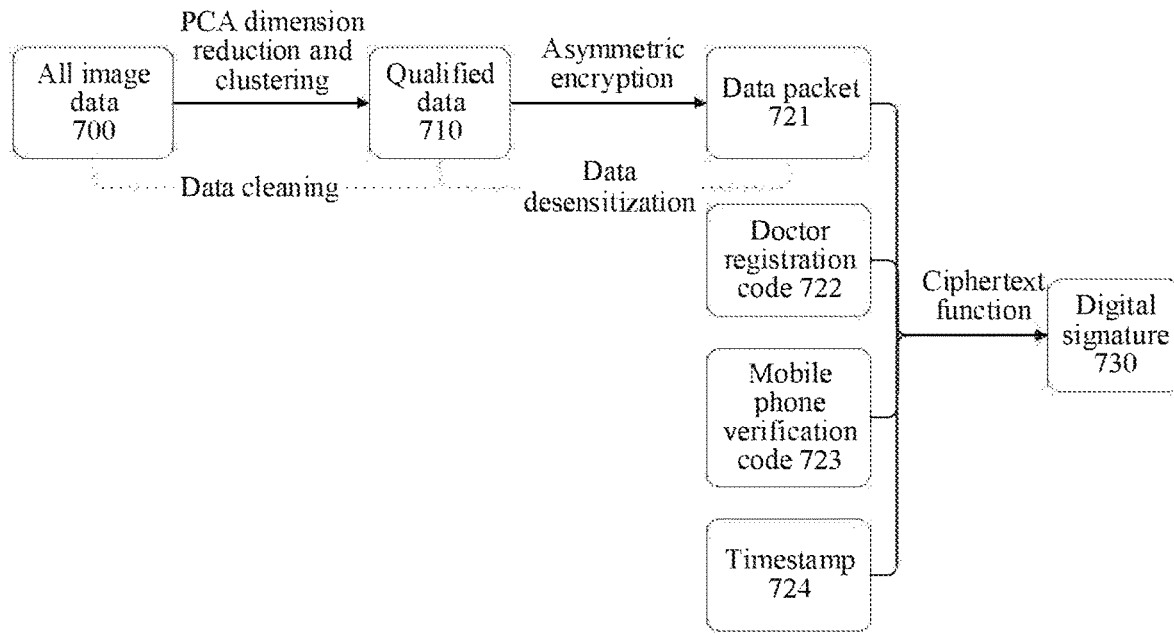
FIG. 7 is a schematic diagram of an image data processing process according to an exemplary embodiment of this disclosure.

For example, referring to FIG. 7, the foregoing target image data is medical image data. FIG. 7 is a schematic diagram of an image data processing process according to an exemplary embodiment of this disclosure. As shown in FIG. 7, after all image data 700 is obtained, PCA dimension reduction and clustering are performed on all the image data 700 for data cleaning to obtain qualified data 710; the qualified data 710 is asymmetrically encrypted for data desensitization of the qualified data 710 to obtain a data packet 721; and the data packet 721, a doctor registration code 722, a doctor mobile phone verification code 723, and a timestamp 724 are signature-encrypted by using a cipher function to obtain a digital signature 730. The digital signature 730 is used for verifying the target image data on the labeling client.

Figure 8:
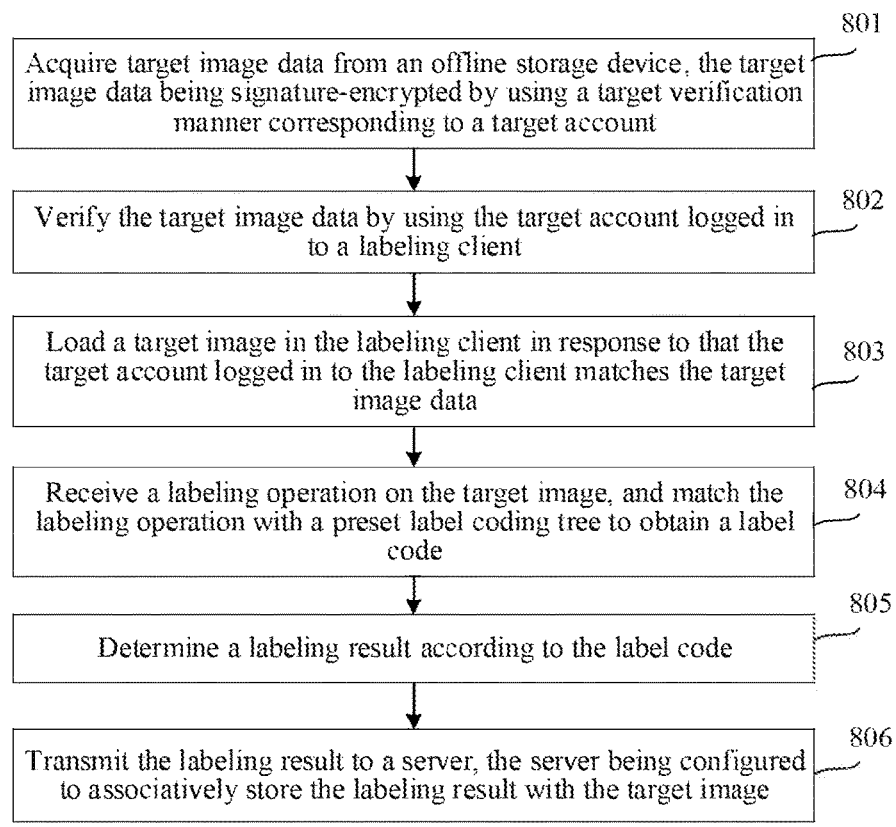
FIG. 8 is a flowchart of a labeling method according to another exemplary embodiment of this disclosure.

In an embodiment, the labeling result is expressed in a code form. FIG. 8 is a flowchart of a labeling method according to another exemplary embodiment of this disclosure. That the method is applied to a terminal is used as an example for description. As shown in FIG. 8, the method can include the following steps.

In step 801, target image data is acquired from an offline storage device, the target image data being signature-encrypted by using a target verification manner corresponding to a target account.

In an embodiment, the target image data is data corresponding to a to-be-labeled target image. After the target image data is encrypted in an encryption manner corresponding to the target account, the target image data is transferred to a current terminal by using the offline storage device.

In an embodiment, the target image data is signature-encrypted by using the target verification manner corresponding to the target account. The target image data can be signature-encrypted by using an encryption function. The encryption function has a verification parameter, a read account specified according to the target image data is the target account, and the verification parameter is related to the target image and the target account. The verification parameter is inputted into the encryption function, so as to perform signature encryption on the target image data. In an embodiment, after signature encryption is performed on the target image data, a digital signature corresponding to the target image data is obtained. The target image data and the digital signature corresponding to the target image data are acquired from the offline storage device.

In step 802, the target image data is verified by using the target account logged in to a labeling client.

In an embodiment, the target verification manner including the foregoing encryption function is used as an example for description. The labeling client inputs, according to the logged-in target account, the target account and an input parameter corresponding to the target image data into the encryption function, to obtain a verification ciphertext on the labeling client side, and after comparing the verification ciphertext with the digital signature corresponding to the target image data, determines whether the target account matches the target image data.

In step 803, the target image is loaded in the labeling client in response to that the target account logged in to the labeling client matches the target image data.

In an embodiment, when the target image data is successfully verified by using the target account logged in to the labeling client, the target image is automatically loaded in the labeling client.

In step 804, a labeling operation on the target image is received, and the labeling operation is matched with a preset label coding tree to obtain a label code.

The label code indicates a preset array or preset character, and the preset array or preset character is manually preset. By using the preset number or preset character to represent the labeling result, the labeling result can be normalized, and a case in which the labeling result does not conform to a requirement is avoided, so that the labeling result has a uniform format, so as to improve labeling accuracy, thereby facilitating secure transmission and structuralization of the labeling result. For example, a preset number is used as an example, and a preset array is "001" corresponding to a labeling result "gastritis".

In an embodiment, the labeling operation may be implemented as a selection operation on the target label in a preset candidate label, or may be implemented as an input operation on the target label according to a preset input rule. This is not limited in this embodiment of this disclosure.

In an embodiment, after the target label to be labeled on the target image is determined according to the labeling operation, the target label is matched with the preset label coding tree to obtain a label code corresponding to the target label.

In a possible implementation, when the labeling operation is a selection operation, that is, a label selection interface is provided in the labeling client, the label selection interface may provide a plurality of label dimensions and dimension candidate values. The labeling person does not need to enter a specific labeling result, and only needs to select, in a corresponding label dimension, a dimension value that matches the target image. Correspondingly, the terminal may automatically match a corresponding label code according to the dimension value, thereby simplifying an operation process of the labeling person.

In an exemplary example, a process of determining the label code according to the selection operation may include the following steps:

1. Obtain, in response to a selection operation for each label dimension indicated by the labeling operation, a dimension value of each label dimension indicated by the selection operation.

The label dimension is related to a field or type to which the target image belongs. For example, if the target image is a medical image, the corresponding label dimension may include each part of the body, that is, the stomach, the eyes, and the leg. If the target image is a plant image, the corresponding label dimension may include a plant type, a name of each part of the plant, and the like. In addition, the label dimension may be divided into different subdimensions based on a labeling requirement. Using a medical image as an example, the label dimension may include a name of a body part and a disease type (name) corresponding to each part, for example, the stomach and a state corresponding to the stomach (normal, gastritis, and gastric cancer).

In a possible implementation, the labeling person may select different label dimensions and dimension values corresponding to the label dimensions from a front end interface of the labeling client. For example, if the labeling person determines, according to the target image, that the target image is a normal stomach image, the labeling person clicks/taps to select a label dimension (a body part and a state of the body part) and a dimension value corresponding to the label dimension (the stomach part and the stomach part being normal), and correspondingly, the terminal obtains the dimension value corresponding to each selection operation.

2. Determine the label code according to the dimension value and the preset label coding tree.

The preset label coding tree may be set based on preset label dimensions and dimension values. For example, a label code "0" is correspondingly set for the stomach part, a label code "0" is correspondingly set and corresponds to a normal state, and a label code "1" is set and corresponds to cancer.

The preset label coding tree may correspond to the label dimension and the dimension value. Therefore, in a possible implementation, a label code indicated by each dimension value may be determined according to the dimension value corresponding to the obtained selection operation and the preset label coding tree.

In an example, if the dimension value is "the stomach part is normal", the label code determined according to the dimension value and the preset label coding tree is "00".

In another possible implementation, to distinguish between different types of target images, different preset label coding trees are preset for different types of target images, so that after labeling is performed, corresponding analysis may be performed according to different label codes (labeling results).

For example, the target image is a medical image, a target medical field corresponding to the medical image is determined, a preset label coding tree corresponding to the target medical field is acquired, and after the target label is matched with the preset label coding tree, a label code is obtained.

Figure 9:
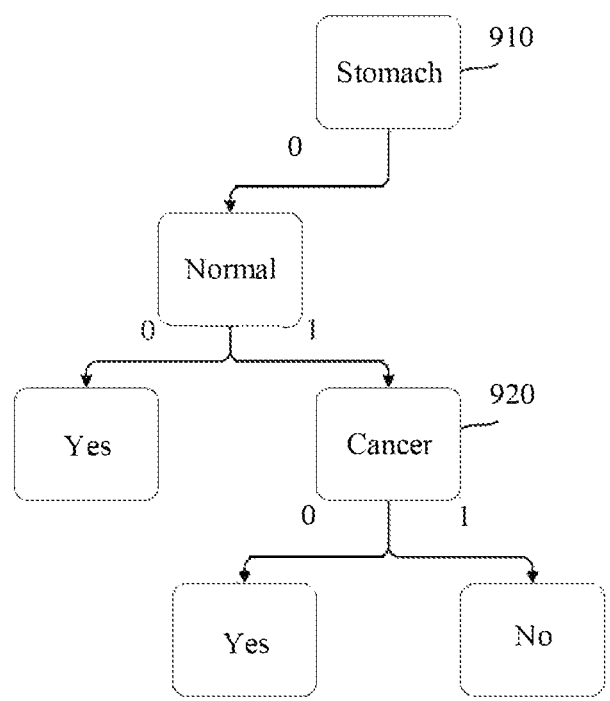
FIG. 9 is a schematic diagram of matching a label with a Huffman coding tree based on the embodiment shown in FIG. 8.

In an embodiment, a label of a medical image has a dependency relationship. For example, a label gastric cancer corresponds to "stomach part, cancer", and the label is combined with a Huffman tree to obtain a Huffman coding tree shown in FIG. 9. For a stomach part 910, a branch is normal. When a value of the normal branch is 0, it indicates that the stomach part 910 is normal. When the value of the normal branch is 1, it indicates that the stomach part 910 is abnormal. When a value of a branch of a cancer 920 is 0, it indicates a label gastric cancer. When the value of the branch of the cancer 920 is 1, it indicates not gastric cancer. Therefore, a code corresponding to the gastric cancer is 010, and a code corresponding to a normal stomach part is 00.

In step 805, a labeling result is determined according to the label code.

In a possible implementation, because the label code is in a uniform format, the label code may be directly used as a labeling result and transmitted back to the server, so that a background person performs quality evaluation and correction on the labeling result.

Because the label code and the target image are uniquely corresponding to each other, to directly determine, on the server side, the target image corresponding to the label code according to the labeling result, in a possible implementation, the label code and the target image data are associated and transmitted back to the server as the labeling result.

In an embodiment, if the labeling result is incorrect, the background person further needs to contact the labeling person in time for modification. To accurately determine a labeling person corresponding to a labeling result, a target account corresponding to the labeling person may be added to the labeling result.

In an embodiment, to consider both a correspondence between the labeling result and the target image, and the labeling person corresponding to the labeling result, in a possible implementation, the target image data and the target account may be used as a combined primary key, and label code is used as a content value to generate the labeling result. The target image data and the target account are used as a combined primary key, so that after the labeling result is transmitted back to the server, the target image corresponding to the labeling result and the labeling person corresponding to the labeling result are accurately determined, so that the background person can conveniently perform quality evaluation and error correction on the labeling result.

In an embodiment, to reduce a data amount transmitted back from the labeling result, in a possible implementation, an image identifier corresponding to the target image may be used as a combined primary key, that is, no target image data needs to be transmitted, and a transmission rate may be further increased.

In step 806, the labeling result is transmitted to a server, the server being configured to associatively store the labeling result with the target image.

The labeling result includes the label code, a digest value corresponding to the target image data, a registration code corresponding to the target account, an image type corresponding to the target image, and the like. The image type corresponding to the target image may be an object name included in the target image. Using a medical image as an example, the image type corresponding to the target image may be a disease name.

In an embodiment, using the target image data being medical image data as an example, for example, a gastric cancer image, it may be determined, according to the foregoing description, that the label code corresponding to the gastric cancer image is "010", a digest value corresponding to the target image data may be a digest value MD5 obtained when the target image data is encrypted, a registration code corresponding to the target account may be a registration code corresponding to a labeling doctor, and an image type may be a disease name or a disease lesion corresponding to the gastric cancer image. For example, for the gastric cancer, the corresponding labeling result includes "101-digest value-registration code-gastric cancer".

Because the labeling result needs to be transmitted back to the server, to facilitate serialized transmission of the labeling result, the labeling result forms a code sequence, after serialization processing is performed, a final labeling result is obtained, and the labeled target image data is transmitted to the server based on a secure shell (SSH) channel.

In conclusion, in the labeling method provided in this embodiment, the target image data is transferred to a terminal in an offline transfer manner, and the target image data is signature-encrypted with reference to the target account logged in to the labeling client in the terminal, so that the target image data can be verified and read only when the account logged in to the labeling client is the target account, and transfer efficiency of the target image data is improved in the offline transfer manner. This avoids a problem that transmission time is too long due to a network speed limitation in an online transfer process, and the signature encryption process improves transfer security of the target image data.

According to the method provided in this embodiment, the preset label coding tree is matched with the labeling operation to obtain the label code as the labeling result, so as to represent the target label received by the target image data, thereby improving labeling efficiency.

Figure 10:
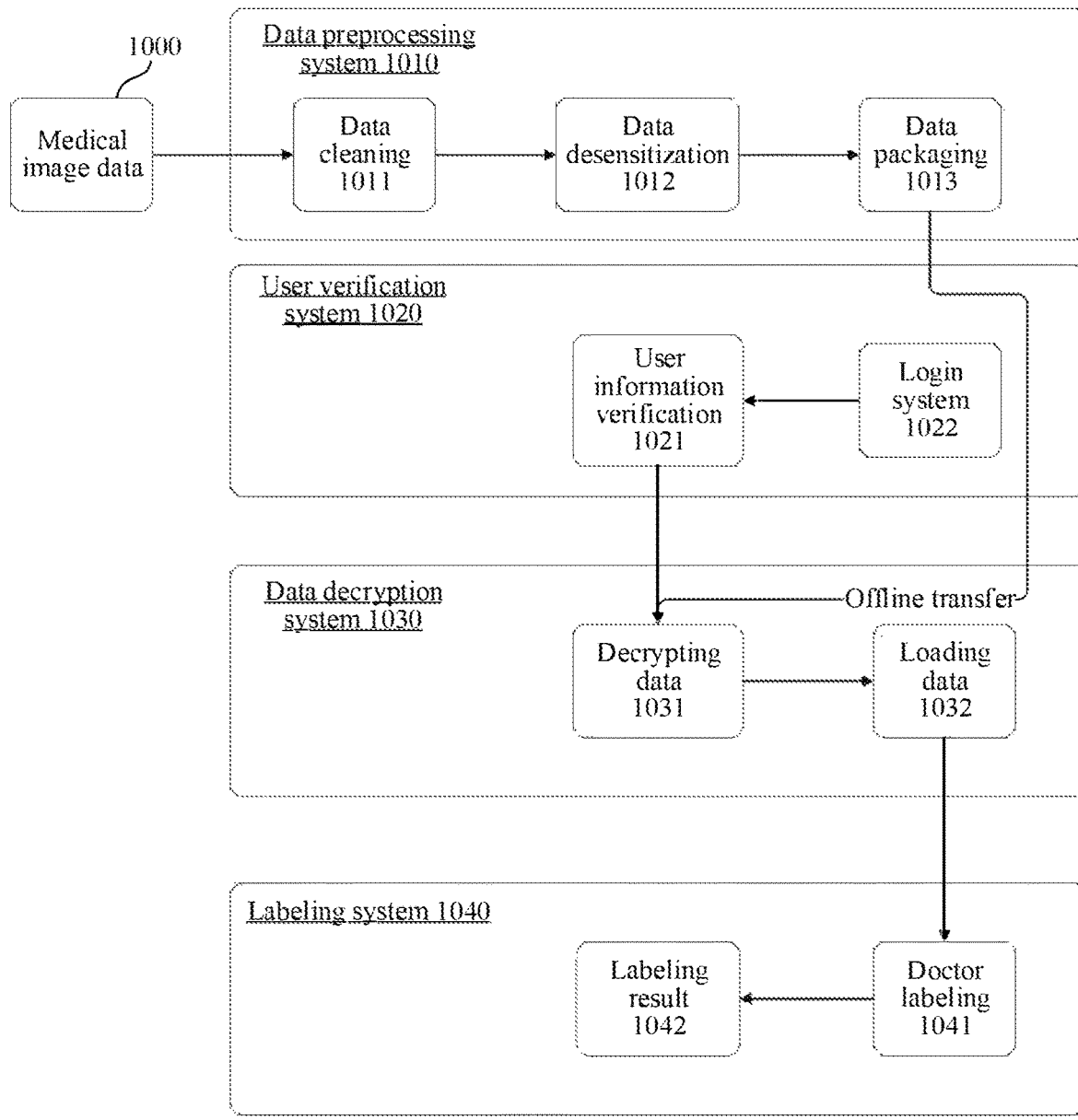
FIG. 10 is an overall schematic diagram of a labeling process of medical image data according to an exemplary embodiment of this disclosure.

For example, FIG. 10 is a schematic diagram of an overall labeling process of medical image data according to an exemplary embodiment of this disclosure. As shown in FIG. 10, the labeling process includes the following four parts: a data preprocessing system 1010, a user verification system 1020, a data decryption system 1030, and a labeling system 1040, so as to label medical image data 1000.

As shown in FIG. 10, the data preprocessing system 1010 includes three parts: data cleaning 1011, data desensitization 1012, and data packaging 1013. First, the medical image data 1000 is inputted into data cleaning 1011 to perform data filtering, to filter out unqualified data or data that does not meet a labeling condition. In an embodiment, based on a related machine learning algorithm, PCA dimension reduction is performed on the image data, the data is clustered with a cosine similarity in vector space, and a threshold is set to filter an image whose edge is abnormal, so as to complete data filtering. Image data that meets a condition is filtered according to a labeling condition of the data. For example, an image whose layer thickness is less than 5 mm is selected according to a thickness of a CT image.

After data cleaning 1011, data desensitization 1012 is performed on the medical image data 1000, and sensitive information of the medical image data 1000 is encrypted and desensitized based on an asymmetric encryption algorithm. Then, data packaging 1013 is performed on the medical image data 1000. In an embodiment, in a data packaging process, signature encryption is performed on MD5 of the medical image data 1000 based on a registration code of a specified labeling doctor, a mobile phone verification code, a timestamp, and a digital signature.

In an embodiment, the user verification system 1020 includes two parts: user information verification 1021 and a login system 1022. After a doctor logs in to the login system 1022, user information verification 1021 is performed according to the doctor's login information.

In a data decryption system 1030, two parts are included: decrypting data 1031 and loading data 1032. The packaged medical image data is decrypted with reference to the login doctor information in the user verification system 1020. Because a labeling doctor corresponding to the login doctor information in the user verification system 1020 is a specified doctor for reading the medical image data, the medical image data can be decrypted and loaded.

In a labeling system 1040, two parts are included: doctor labeling 1041 and obtaining a labeling result 1042, that is, the doctor performs a labeling operation with reference to the loaded medical image data, to obtain a labeling result.

In conclusion, in the labeling method provided in this embodiment, the target image data is transferred to a terminal in an offline transfer manner, and the target image data is signature-encrypted with reference to the target account logged in to the labeling client in the terminal, so that the target image data can be verified and read only when the account logged in to the labeling client is the target account, and transfer efficiency of the target image data is improved in the offline transfer manner. This avoids a problem that transmission time is too long due to a network speed limitation in an online transfer process, and the signature encryption process improves transfer security of the target image data in the offline transfer process.

Figure 11:
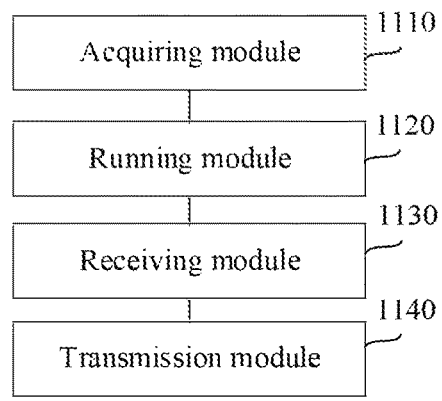
FIG. 11 is a structural block diagram of a labeling apparatus according to an exemplary embodiment of this disclosure.

FIG. 11 is a structural block diagram of a labeling apparatus according to an exemplary embodiment of this disclosure. As shown in FIG. 11, the apparatus includes an acquiring module 1110, a running module 1120, a receiving module 1130, and a transmission module 1140. One or more modules, submodules, and/or units of the apparatus can be implemented by processing circuitry, software, or a combination thereof, for example.

The acquiring module 1110 is configured to acquire target image data from an offline storage device, the target image data being data corresponding to a to-be-labeled target image, and the target image data being signature-encrypted by using a target verification manner corresponding to a target account.

The running module 1120 is configured to verify the target image data by using the target account logged in to a labeling client; and load the target image in the labeling client in response to that the target account logged in to the labeling client matches the target image data.

The receiving module 1130 is configured to receive a labeling operation on the target image, to obtain a labeling result of the target image.

The transmission module 1140 is configured to transmit the labeling result to a server, the server being configured to associatively store the labeling result with the target image.

In an embodiment, the target image data further correspondingly has a digital signature, the target verification manner includes an encryption function, and the encryption function corresponds to an input parameter.

Figure 12:
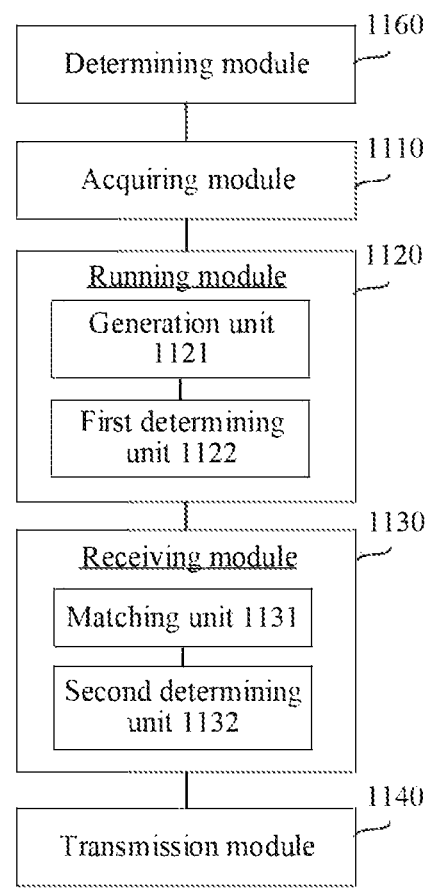
FIG. 12 is a structural block diagram of a labeling apparatus according to another exemplary embodiment of this disclosure.

As shown in FIG. 12, the running module 1120 can include a generation unit 1121 and a first determining unit 1122.

The generation unit 1121 is configured to input the input parameter into the encryption function to generate a verification ciphertext.

The first determining unit 1122 is configured to determine, in response to the digital signature matching the verification ciphertext, that the target account matches the target image data.

In an embodiment, the input parameter includes at least one of an account parameter corresponding to the target account and an image parameter corresponding to the target image data.

The account parameter includes at least one of a registration code of the target account and a verification code for the target account to bind a communication contact number.

The image parameter includes at least one of a generation timestamp of the digital signature corresponding to the target image data and a digest value of the target image data.

In an embodiment, the input parameter includes the account parameter and the image parameter, the account parameter includes the registration code of the target account and the verification code for the target account to bind the communication contact number, and the image parameter includes the generation timestamp of the digital signature and the digest value of the target image data.

The generation unit 1121 is further configured to input the registration code of the target account, the verification code for the target account to bind the communication contact number, the digest value of the target image data, and the generation timestamp of the digital signature into the encryption function to obtain the verification ciphertext.

In an embodiment, the receiving module 1130 further includes a matching unit 1131 and a second determining unit 1132.

The matching unit 1131 is configured to match the labeling operation with a preset label coding tree to obtain a label code. The second determining unit 1132 is configured to determine the labeling result according to the label code.

In an embodiment, the matching unit 1131 is further configured to obtain, in response to a selection operation for each label dimension indicated by the labeling operation, a dimension value of each label dimension indicated by the selection operation. The matching unit 1131 is further configured to determine the label code according to the dimension value and the preset label coding tree.

In an embodiment, the target image includes a medical image and the apparatus further includes a determining module 1160. The determining module 1160 is configured to determine a target medical field corresponding to the medical image. The acquiring module 1110 is further configured to acquire the preset label coding tree corresponding to the target medical field.

In an embodiment, the second determining unit 1132 is further configured to: generate the labeling result by using the target image data and the target account as a combined primary key value and using the label code as a content value.

In an embodiment, the target image data is image data obtained through preprocessing, and the preprocessing process includes at least one of data filtering, data desensitization, and data structuralization.

In conclusion, in the labeling apparatus provided in this embodiment, the target image data is transferred to a terminal in an offline transfer manner, and the target image data is signature-encrypted with reference to the target account logged in to the labeling client in the terminal, so that the target image data can be verified and read only when the account logged in to the labeling client is the target account, and transfer efficiency of the target image data is improved in the offline transfer manner. This can avoid a problem that transmission time is too long due to a network speed limitation in an online transfer process, and the signature encryption process can improve transfer security of the target image data in the offline transfer process.

The labeling apparatus provided in the foregoing embodiments is illustrated with an example of division of the foregoing functional modules. In actual application, the functions may be allocated to and completed by different functional modules according to requirements, that is, the internal structure of the device is divided into different functional modules, to implement all or some of the functions described above. In addition, the labeling apparatus and method embodiments provided in the foregoing embodiments belong to the same concept. For the specific implementation process, reference may be made to the method embodiments, and details are not described herein again.

The term module (and other similar terms such as unit, submodule, etc.) in this disclosure may refer to a software module, a hardware module, or a combination thereof. A software module (e.g., computer program) may be developed using a computer programming language. A hardware module may be implemented using processing circuitry and/or memory. Each module can be implemented using one or more processors (or processors and memory). Likewise, a processor (or processors and memory) can be used to implement one or more modules. Moreover, each module can be part of an overall module that includes the functionalities of the module.

Figure 13:
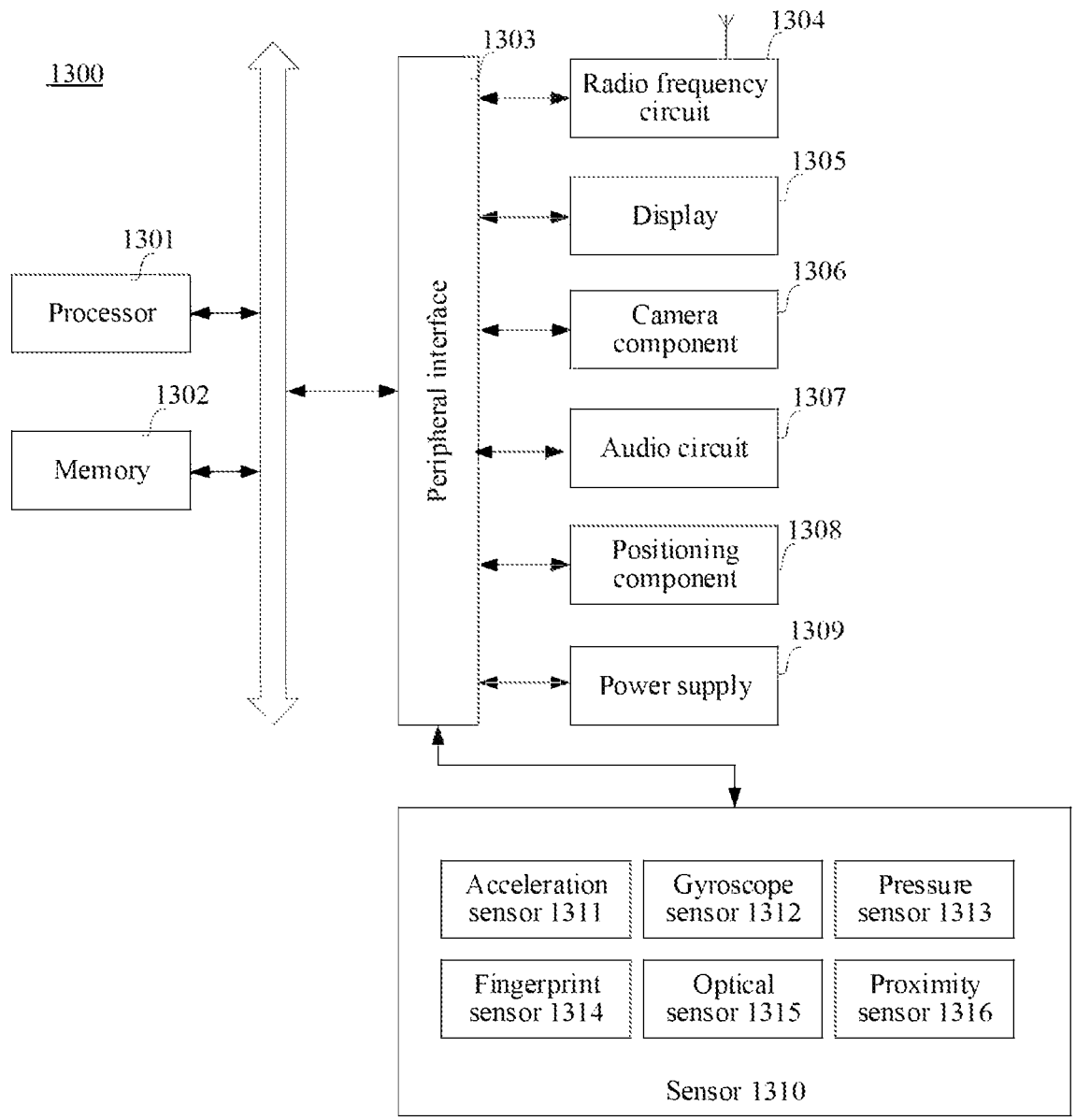
FIG. 13 is a structural block diagram of a terminal according to an exemplary embodiment of this disclosure.

FIG. 13 is a structural block diagram of a terminal 1300 according to an exemplary embodiment of the present disclosure. The terminal 1300 may be a smartphone, a tablet computer, an MP3 player, an MP4 player, a notebook computer, or a desktop computer. The terminal 1300 may also be referred to as user equipment, a portable terminal, a laptop terminal, or a desktop terminal, among other names.

Generally, the terminal 1300 includes processing circuitry, such as a processor 1301, and a memory 1302.

The processor 1301 may include one or more processing cores. For example, the processor 1301 may be a 4-core processor or an 8-core processor. The processor 1301 may be implemented in at least one hardware form of digital signal processing (DSP), a field programmable gate array (FPGA), and a programmable logic array (PLA). The processor 1301 may alternatively include a main processor and a coprocessor. The main processor is configured to process data in an active state, also referred to as a central processing unit (CPU). The coprocessor is a low-power processor configured to process data in a standby state. In some embodiments, the processor 1301 may be integrated with a graphics processing unit (GPU). The GPU is configured to render and draw content that needs to be displayed on a display. In some embodiments, the processor 1301 may further include an artificial intelligence (AI) processor. The AI processor is configured to process a computing operation related to machine learning.

The memory 1302 may include one or more computer-readable storage media that may be non-transitory. The memory 1302 may further include a high-speed random access memory (RAM) and a nonvolatile memory, for example, one or more disk storage devices or flash storage devices. In some embodiments, a non-transitory computer-readable storage medium in the memory 1302 is configured to store at least one instruction, the at least one instruction being configured to be executed by the processor 1301 to implement the labeling method provided in the method embodiments of this disclosure.

In some embodiments, the terminal 1300 may include a peripheral interface 1303 and at least one peripheral. The processor 1301, the memory 1302, and the peripheral interface 1303 may be connected by using a bus or a signal cable. Each peripheral device may be connected to the peripheral device interface 1303 by using a bus, a signal cable, or a circuit board. Specifically, the peripheral device includes: at least one of a radio frequency (RF) circuit 1304, a display screen 1305, a camera component 1306, an audio circuit 1307, a positioning component 1308, and a power supply 1309.

The peripheral interface 1303 may be configured to connect at least one peripheral device related to I/O to the processor 1301 and the memory 1302. In some embodiments, the processor 1301, the memory 1302, and the peripheral interface 1303 are integrated on the same chip or the same circuit board. In some other embodiments, any or both of the processor 1301, the memory 1302, and the peripheral interface 1303 may be implemented on an independent chip or circuit board. This is not limited in this embodiment.

The RF circuit 1304 is configured to receive and transmit an RF signal, which is also referred to as an electromagnetic signal. The RF circuit 1304 communicates with a communication network and other communication devices through the electromagnetic signal. The radio frequency circuit 1304 converts an electrical signal into an electromagnetic signal for transmission, or converts a received electromagnetic signal into an electrical signal. In some embodiments, the RF circuit 1304 includes: an antenna system, an RF transceiver, one or more amplifiers, a tuner, an oscillator, a digital signal processor, a codec chip set, a subscriber identity module card, and the like. The RF circuit 1304 may communicate with another terminal by using at least one wireless communication protocol. The wireless communication protocol includes, but is not limited to, a world wide web, a metropolitan area network, an intranet, generations of mobile communication networks (2G, 3G, 4G, and 5G), a wireless local area network and/or a Wi-Fi network. In some embodiments, the RF circuit 1304 may further include a circuit related to NFC, which is not limited in this disclosure.

The display screen 1305 is configured to display a user interface (UI). The UI may include a graph, a text, an icon, a video, and any combination thereof. When the display screen 1305 is a touchscreen, the display screen 1305 is further capable of acquiring a touch signal on or above a surface of the display screen 1305. The touch signal may be used as a control signal to be inputted to the processor 1301 for processing. In this case, the display screen 1305 may be further configured to provide a virtual button and/or a virtual keyboard that are/is also referred to as a soft button and/or a soft keyboard. In some embodiments, there may be one display screen 1305, disposed on a front panel of the terminal 1300. In other embodiments, there may be at least two display screens 1305 that are respectively disposed on different surfaces of the terminal 1300 or folded. In still other embodiments, the display screen 1305 may be a flexible display screen disposed on a curved surface or a folded surface of the terminal 1300. Even, the display screen 1305 may be further set to have a non-rectangular irregular graph, that is, a special-shaped screen. The display screen 1305 may be prepared by using materials such as a liquid-crystal display (LCD), an organic light-emitting diode (OLED), or the like.

The camera assembly 1306 is configured to acquire an image or a video. For example, the camera assembly 1306 includes a front-facing camera and a rear-facing camera. Generally, the front-facing camera is disposed on the front panel of the terminal, and the rear-facing camera is disposed on a back surface of the terminal. In some embodiments, there are at least two rear cameras, which are respectively any of a main camera, a depth-of-field camera, a wide-angle camera, and a telephoto camera, to implement background blur through fusion of the main camera and the depth-of-field camera, panoramic photographing and virtual reality (VR) photographing through fusion of the main camera and the wide-angle camera, or other fusion photographing functions. In some embodiments, the camera assembly 1306 may further include a flash. The flashlight may be a monochrome temperature flashlight, or may be a double color temperature flashlight. The double-color-temperature flash refers to a combination of a warm-light flash and a cold-light flash, and may be used for light compensation under different color temperatures.

The audio circuit 1307 may include a microphone and a loudspeaker. The speaker is configured to acquire sound waves of a user and an environment, and convert the sound waves into electric signals and input the electrical signals into the processor 1301 for processing, or input the electrical signals into the RF circuit 1304 to implement speech communication. For the purpose of stereo sound acquisition or noise reduction, there may be a plurality of microphones, respectively disposed at different parts of the terminal 1300. The microphone may further be an array microphone or an omni-directional acquisition type microphone. The loudspeaker is configured to convert electric signals from the processor 1301 or the RF circuit 1304 into sound waves. The loudspeaker may be a conventional thin-film loudspeaker or a piezoelectric ceramic loudspeaker. When the speaker is the piezoelectric ceramic speaker, the speaker can not only convert an electrical signal into sound waves audible to a human being, but also convert an electrical signal into sound waves inaudible to the human being for ranging and other purposes. In some embodiments, the audio circuit 1307 may also include an earphone jack.

The positioning component 1308 is configured to position a current geographic position of the terminal 1300, to implement navigation or a location based service (LBS). The positioning component 1308 may be a positioning assembly based on the Global Positioning System (GPS) of the United States, the China's Beidou Navigation Satellite System (BDS), or the Galileo system of Russia.

The power supply 1309 is configured to supply power to assemblies in the terminal 1300. The power supply 1309 may be an alternating-current power supply, a direct-current power supply, a disposable battery, or a rechargeable battery. When the power supply 1309 includes a rechargeable battery, the rechargeable battery may be a wired rechargeable battery or a wireless rechargeable battery. The wired rechargeable battery is a battery charged through a wired circuit, and the wireless rechargeable battery is a battery charged through a wireless coil. The rechargeable battery may be further configured to support a fast charge technology.

In some embodiments, the terminal 1300 may also include one or more sensors 1310. The one or more sensors 1310 include, but are not limited to, an acceleration sensor 1311, a gyroscope sensor 1312, a pressure sensor 1313, a fingerprint sensor 1314, an optical sensor 1315, and a proximity sensor 1316.

The acceleration sensor 1311 may detect a magnitude of acceleration on three coordinate axes of a coordinate system established with the terminal 1300. For example, the acceleration sensor 1311 may be configured to detect components of gravity acceleration on the three coordinate axes. The processor 1301 may control, according to a gravity acceleration signal collected by the acceleration sensor 1311, the display screen 1305 to display the user interface in a frame view or a portrait view. The acceleration sensor 1311 may be further configured to acquire motion data of a game or a user.

The gyroscope sensor 1312 may detect a body direction and a rotation angle of the terminal 1300, and the gyroscope sensor 1312 may work with the acceleration sensor 1311 to collect a 3D action performed by the user on the terminal 1300. The processor 1301 may implement the following functions according to the data acquired by the gyroscope sensor 1312: motion sensing (such as changing the UI according to a tilt operation of the user), image stabilization at shooting, game control, and inertial navigation.

The pressure sensor 1313 may be disposed at a side frame of the terminal 1300 and/or a lower layer of the display screen 1305. When the pressure sensor 1313 is disposed at the side frame of the terminal 1300, a holding signal of the user on the terminal 1300 may be detected. The processor 1301 performs left/right hand recognition or a quick operation according to the holding signal acquired by the pressure sensor 1313. When the pressure sensor 1313 is disposed on the low layer of the display screen 1305, the processor 1301 controls, according to a pressure operation of the user on the display screen 1305, an operable control on the UI. The operable control includes at least one of a button control, a scroll-bar control, an icon control, and a menu control.

The fingerprint sensor 1314 is configured to acquire a fingerprint of a user, and the processor 1301 recognizes an identity of the user according to the fingerprint acquired by the fingerprint sensor 1314, or the fingerprint sensor 1314 recognizes the identity of the user based on the acquired fingerprint. When identifying that the identity of the user is a trusted identity, the processor 1301 authorizes the user to perform related sensitive operations. The sensitive operations include: unlocking a screen, viewing encryption information, downloading software, paying and changing a setting, and the like. The fingerprint sensor 1314 may be disposed on a front surface, a back surface, or a side surface of the terminal 1300. When a physical button or a vendor logo is disposed on the terminal 1300, the fingerprint 1314 may be integrated with the physical button or the vendor logo.

The optical sensor 1315 is configured to collect ambient light intensity. In an embodiment, the processor 1301 may control display luminance of the display screen 1305 according to the ambient light intensity collected by the optical sensor 1315. Specifically, when the ambient light intensity is relatively high, the display brightness of the display 1305 is increased. When the ambient light intensity is relatively low, the display brightness of the display screen 1305 is reduced. In another embodiment, the processor 1301 may further dynamically adjust a camera parameter of the camera assembly 1306 according to the ambient light intensity acquired by the optical sensor 1315.

The proximity sensor 1316, also referred to as a distance sensor, is usually disposed on the front panel of the terminal 1300. The proximity sensor 1316 is configured to acquire a distance between the user and the front surface of the terminal 1300. In an embodiment, when the proximity sensor 1316 detects that the distance between the user and the front surface of the terminal 1300 gradually becomes small, the touch display screen 1305 is controlled by the processor 1301 to switch from a screen-on state to a screen-off state. When the proximity sensor 1316 detects that the distance between the user and the front surface of the terminal 1300 gradually increases, the display screen 1305 is controlled by the processor 1301 to switch from the screen-off state to the screen-on state.

A person skilled in the art can understand that the structure shown in FIG. 13 is exemplary and does not constitute a limitation on the terminal 1300, more or fewer assemblies may be included as compared with the figure, some assemblies may be combined, or different assemblies may be adopted for arrangement.

An embodiment of this disclosure further provides a computer readable storage medium, storing at least one segment of program, and the at least one segment of program being loaded and executed by a processor to implement the labeling method described in foregoing embodiments.

The computer-readable storage medium may include: a read-only memory (ROM), a random access memory (RAM), a solid state drive (SSD), an optical disc, or the like. The RAM may include a resistance random access memory (ReRAM) and a dynamic random access memory (DRAM). The sequence numbers of the foregoing embodiments of this disclosure are merely for description purpose, and are not intended to indicate priorities of the embodiments.

An embodiment of this disclosure provides a computer program product or a computer program. The computer program product or the computer program includes computer instructions, and the computer instructions are stored in a computer-readable storage medium. A processor of a computer device reads the computer instructions from the computer-readable storage medium, and executes the computer instructions, so that the computer device performs the labeling method provided in the foregoing optional implementations.

A person of ordinary skill in the art may understand that all or some of the steps of the foregoing embodiments may be implemented by hardware, or may be implemented by a program instructing related hardware. The program may be stored in a computer-readable storage medium such as a non-transitory computer-readable storage medium. The storage medium may be a ROM, a magnetic disk, or an optical disc.

The foregoing descriptions are merely exemplary embodiments of this disclosure, but are not intended to limit this disclosure. Any modification, equivalent replacement, or improvement made within the spirit and principle of this disclosure shall fall within the protection scope of this disclosure.

What is claimed is:

1. A labeling method, comprising:
    acquiring target image data of a target image from an offline storage device, the target image data being encrypted based on a first target account;
    verifying a permission to load the target image data based on a second target account logged in to a labeling client;
    loading, by processing circuitry, the target image in the labeling client in response to the permission to load the target image being verified when the second target account logged in to the labeling client matches the first target account;
    receiving a label for the target image; and
    transmitting the label for the target image to a server, the server being configured to store the label in association with the target image.

2. The method according to claim 1, wherein the verifying comprises:
    inputting an input parameter of the target image data and the second target account into an encryption function to generate a verification ciphertext; and
    verifying, in response to a digital signature of the target image data matching the verification ciphertext, the permission to load the target image data.

3. The method according to claim 2, wherein
    the input parameter includes at least one of an account parameter corresponding to the second target account or an image parameter corresponding to the target image data;
    the account parameter includes at least one of a registration code of the second target account and a verification code for the second target account to bind a communication contact number; and
    the image parameter includes at least one of a generation timestamp of the digital signature corresponding to the target image data and a digest value of the target image data.

4. The method according to claim 3, wherein the input parameter includes the account parameter and the image parameter, the account parameter includes the registration code of the second target account and the verification code for the second target account to bind the communication contact number, and the image parameter includes the generation timestamp of the digital signature and the digest value of the target image data; and
    the inputting the input parameter into the encryption function comprises:
    inputting the registration code of the second target account, the verification code for the second target account to bind the communication contact number, the digest value of the target image data, and the generation timestamp of the digital signature into the encryption function to obtain the verification ciphertext.

5. The method according to claim 1, wherein the receiving the label comprises:
    matching a labeling operation with a preset label coding tree to obtain a label code; and
    determining the label according to the label code.

6. The method according to claim 5, wherein the matching the labeling operation comprises:
    obtaining, in response to a selection operation for each label dimension indicated by the labeling operation, a dimension value of each label dimension indicated by the selection operation; and
    determining the label code according to the dimension value and the preset label coding tree.

7. The method according to claim 5, wherein
    the target image includes a medical image; and
    before the matching the labeling operation, the method further comprises:
    determining which of a plurality of label coding trees corresponds to the medical image; and
    acquiring the determined label coding tree corresponding to a target medical field.

8. The method according to claim 5, wherein the determining the label comprises:
    determining the label based on the target image data and the second target account as a combined primary key value and using the label code as a content value.

9. The method according to claim 1, wherein
    the target image data is obtained through preprocessing, and the preprocessing includes at least one of data filtering, data desensitization, and data structuralization.

10. A labeling apparatus, comprising:
    processing circuitry configured to:
    acquire target image data of a target image from an offline storage device, the target image data being encrypted based on a first target account;
    verify a permission to load the target image data based on a second target account logged in to a labeling client;
    load the target image in the labeling client in response to the permission to load the target image being verified when the second target account logged in to the labeling client matches the first target account;
    receive a label for the target image; and
    transmit the label for the target image to a server, the server being configured to store the label in association with the target image.

11. The labeling apparatus according to claim 10, wherein the processing circuitry is configured to:
  input an input parameter of the target image data and the second target account into an encryption function to generate a verification ciphertext; and
  verify, in response to a digital signature of the target image data matching the verification ciphertext, the permission to load the target image data.

12. The labeling apparatus according to claim 11, wherein
  the input parameter includes at least one of an account parameter corresponding to the second target account or an image parameter corresponding to the target image data;
  the account parameter includes at least one of a registration code of the second target account and a verification code for the second target account to bind a communication contact number; and
  the image parameter includes at least one of a generation timestamp of the digital signature corresponding to the target image data and a digest value of the target image data.

13. The labeling apparatus according to claim 12, wherein the input parameter includes the account parameter and the image parameter, the account parameter includes the registration code of the second target account and the verification code for the second target account to bind the communication contact number, and the image parameter includes the generation timestamp of the digital signature and the digest value of the target image data; and
  the processing circuitry is configured to input the registration code of the second target account, the verification code for the second target account to bind the communication contact number, the digest value of the target image data, and the generation timestamp of the digital signature into the encryption function to obtain the verification ciphertext.

14. The labeling apparatus according to claim 10, wherein the processing circuitry is configured to:
  match a labeling operation with a preset label coding tree to obtain a label code; and
  determine the label according to the label code.

15. The labeling apparatus according to claim 14, wherein the processing circuitry is configured to:
  obtain, in response to a selection operation for each label dimension indicated by the labeling operation, a dimension value of each label dimension indicated by the selection operation; and
  determine the label code according to the dimension value and the preset label coding tree.

16. The labeling apparatus according to claim 14, wherein the target image includes a medical image; and
  before the labeling operation is matched, the processing circuitry is configured to:
    determine which of a plurality of label coding trees corresponds to the medical image; and
    acquire the determined label coding tree corresponding to a target medical field.

17. The labeling apparatus according to claim 14, wherein the processing circuitry is configured to:
  determine the label based on the target image data and the second target account as a combined primary key value and using the label code as a content value.

18. The labeling apparatus according to claim 10, wherein the target image data is obtained through preprocessing, and the preprocessing includes at least one of data filtering, data desensitization, and data structuralization.

19. A non-transitory computer-readable storage medium storing instructions which when executed by a processor cause the processor to perform:
  acquiring target image data of a target image from an offline storage device, the target image data being encrypted based on a first target account;
  verifying a permission to load the target image data based on a second target account logged in to a labeling client;
  loading the target image in the labeling client in response to the permission to load the target image being verified when the second target account logged in to the labeling client matches the first target account;
  receiving a label for the target image; and
  transmitting the label for the target image to a server, the server being configured to store the label in association with the target image.

20. The non-transitory computer-readable storage medium according to claim 19, wherein the verifying comprises:
  inputting an input parameter of the target image data and the second target account into an encryption function to generate a verification ciphertext; and
  verifying, in response to a digital signature of the target image data matching the verification ciphertext, the permission to load the target image data.

* * * * *